United States Patent [19]

Selwitz et al.

[11] 4,158,664

[45] Jun. 19, 1979

[54] PROCESS FOR IMPROVING COLOR OF CERTAIN ALKENYL SUCCINIC ANHYDRIDES

[75] Inventors: Charles M. Selwitz, Monroeville; Helen I. Thayer, Oakmont, both of Pa.

[73] Assignee: Gulf Research & Development Company, Pittsburgh, Pa.

[21] Appl. No.: 807,369

[22] Filed: Jun. 17, 1977

[51] Int. Cl.$^2$ .................... C07D 307/60; C07C 51/00
[52] U.S. Cl. .............................. 260/346.74; 562/593; 562/595
[58] Field of Search ...................... 260/346.74, 537 N

[56] References Cited

U.S. PATENT DOCUMENTS

| | | | |
|---|---|---|---|
| 2,230,005 | 1/1941 | Moser | 260/537 N |
| 4,071,581 | 1/1978 | Yokoyama | 260/346.74 |

FOREIGN PATENT DOCUMENTS 2263547  7/1973  Fed. Rep. of Germany ...... 260/537 N

OTHER PUBLICATIONS

Wagner et al., Synthetic Organic Chemistry, John Wiley (1953), pp. 558–559.

*Primary Examiner*—John M. Ford
*Assistant Examiner*—Bernard Dentz

[57] ABSTRACT

A process for improving the color of crude alkenyl succinic anhydrides which comprises treating said anhydrides with water.

5 Claims, No Drawings

PROCESS FOR IMPROVING COLOR OF CERTAIN ALKENYL SUCCINIC ANHYDRIDES

BACKGROUND OF THE INVENTION

1. Field of the Invention

This invention relates to a process for improving the color of crude alkenyl succinic anhydrides prepared from the reaction of maleic anhydride with olefins which comprises treating said alkenyl succinic anhydrides with water.

2. Description of the Prior Art

Alkenyl succinic anhydrides can be obtained by reacting maleic anhydride with alpha olefins. Unfortunately, the alkenyl succinic anhydrides so produced are dark in color. When such anhydrides are utilized, for example, by incorporating the same in paraffin waxes to increase the hardness thereof, the resulting composition is also dark in color and therefore possesses little commercial appeal.

SUMMARY OF THE INVENTION

We have found that the color of crude alkenyl succinic anhydrides prepared from the reaction of maleic anhydride with olefins can be substantially improved by treating said crude alkenyl succinic anhydrides with water.

Any conventional procedure known in the art can be employed in preparing the alkenyl succinic anhydrides treated herein. One procedure for preparing such compounds could involve reacting, with stirring, a mixture of a straight or branched olefin and maleic anhydride at a molar ratio of olefin to maleic anhydride of about 0.5:1 to about 2:1, preferably about 0.8:1 to about 1.25:1 at a temperature of about 140° to about 250° C., preferably about 180° to about 220° C., and a pressure of about 0.1 to about 1000 pounds per square inch gauge (about 0.007 to about 70.3 kilograms per square centimeter), preferably about 10 to about 20 pounds per square inch gauge (about 0.7 to about 1.4 kilograms per square centimeter), for about three to about 60 hours, preferably about six to about 24 hours. The olefin, or mixture of olefins, used will be straight or branched chain, but preferably straight, having from 26 to 100 carbon atoms, preferably from 30 to 60 carbon atoms. These olefins can be obtained from any suitable source, but preferably are obtained by polymerizing ethylene in the presence of an aluminum alkyl catalyst, for example, as in U.S. Pat. No. 3,482,000 to Fernald et al, or by cracking petroleum stocks, and paraffinic materials, such as microcrystalline wax and polyethylene. To separate any unreacted components that may be present the reaction mixture can be subjected to distillation at a temperature of about 150° to about 250° C., preferably about 180° C. to about 220° C., and a pressure of about 0.01 to about 10 pounds per square inch gauge (about 0.0007 to about 0.7 kilograms per square centimeter), preferably about 0.1 to about 0.5 pounds per square inch gauge (about 0.007 to about 0.035 kilograms per square centimeter).

The alkenyl succinic anhydride obtained herein can be one having the following structural formula:

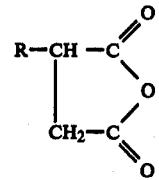

wherein R is an alkenyl group, straight or branched chain, but preferably straight, having from 26 to 100 carbon atoms, preferably from 30 to 60 carbon atoms.

As noted above, the alkenyl succinic anhydride obtained above is dark in color. In order to improve the color of said alkenyl succinic anhydride, the same is treated with water under specified conditions fully set forth below.

The treatment involves bringing together the alkenyl succinic anhydride, prepared as defined above, at a temperature of about 75° to about 150° C., preferably about 90° to about 120° C., with water at a temperature of about 0° to about 80° C., preferably about 5° to about 40° C., while mechanically stirring the mixture until the temperature of the resulting mixture results in the solidification of the alkenyl succinic compound, which becomes converted to the corresponding alkenyl succinic acid, in particulate form. In a preferred embodiment the alkenyl succinic anhydride product in molten form is poured into water. The temperature of the water at this point will be in the range of about 10° to about 80° C., generally about 20° to about 40° C. after a period of stirring of about one-half to about three hours, generally about one to about two hours. Although this treatment is preferably carried out at about ambient pressure, the pressure can range from about five to about 1000 pounds per square inch gauge (about 0.35 to about 70 kilograms per square centimeter), preferably about 10 to about 20 pounds per square inch gauge (about 0.7 to about 1.4 kilograms per square centimeter). The amount of water needed for purification can vary over a wide range and can be, for example, on a molar basis relative to the crude reaction product from about 10:1 to about 1000:1, but preferably in the range of about 50:1 to about 500:1. Following this treatment the solid product and the water are separated from each other by any suitable mechanical means, for example, by filtration, centrifugation, etc. If desired the treatment procedure defined above can be repeated in order to further improve the color of the solids and/or the solids can be washed with additional water to remove color bodies adsorbed on the surface thereof. As noted, at the end of the defined treatment the alkenyl succinic anhydride will have had its color improved, but it will also have been converted to the corresponding alkenyl succinic acid. To convert the latter to the original alkenyl succinic anhydride, any conventional dehydration procedure can be used. For example, the alkenyl succinic acid can be heated at a temperature of about 80° to about 250° C., preferably about 100° to about 200° C., and a pressure of about 0.01 to about 30 pounds per square inch gauge (about 0.0007 to about 2.1 kilograms per square centimeter), preferably about one to about 15 pounds per square inch gauge (about 0.07 to about 1.05 kilograms per square centimeter) for about 0.5 to about 100 hours, preferably about two to about 50 hours.

DESCRIPTION OF PREFERRED EMBODIMENTS

The purification procedure defined and claimed herein can further be described by the following examples. The alpha olefin mixture used in the examples was a fraction obtained from the product resulting from the telomerization of ethylene in the presence of triethyl aluminum at a temperature of about 200° C. and a pressure of about 3400 pounds per square inch gauge (about 239 kilograms per square centimeter) over a period of 30–60 minutes and is further defined below in Table I.

TABLE I

| Isomer Distribution | Per Cent by Weight |
|---|---|
| Vinyl | 70.9 |
| Vinylidene | 20.6 |
| Cis | 2.1 |
| Trans | 4.3 |
| Saturates | 2.0 |
| Iodine Number | 47.3 |
| Average Molecular Weight | 529 (corresponds to 37.8C) |
| Penetration, ASTM, D1321 | 12 (25° C.) |
|  | 28 (38° C.) |
| Color, Saybolt, ASTM D156 | +16 (white) |
| Melting Range, °C. | 55–75 |

EXAMPLE I

A mixture of 397 grams of the specific alpha olefin fraction defined above and 83.3 grams of maleic anhydride were stirred and heated at a temperature of about 193° to 200° C. and ambient pressure in a nitrogen atmosphere for 16 hours. The pressure of the reaction mixture was then reduced to about 5 to 10 millimeters of mercury and distilled to recover the unreacted maleic anhydride, which amounted to 16.6 grams. The remaining mixture was cooled to 100° C. and poured into 0.5 liter of water while stirring. The resulting mixture was stirred for one hour and reached a temperature of 65° C. The wash water, which was very dark in color, was decanted and replaced with two liters of water. The mixture was heated with stirring at 77° C. for 30 minutes, at which point the product (a granulated solid) became tacky. The water was light amber in color. The product was stirred and cooled to 50° C., filtered and then washed with cold water until the wash water was colorless and tested neutral to pH paper. There was obtained 422 grams of a light amber alkenyl succinic acid.

EXAMPLE II

To 1985 parts of the alpha olefin mixture defined above in a closed flask there was added 404.3 grams of maleic anhydride. At ambient pressure the mixture was heated with stirring to 85° C., flushed with nitrogen and the temperature was raised to 200° to 210° C. After a twenty-hour period, the pressure was reduced to 10 millimeters of mercury and 58.7 grams of maleic anhydride was recovered. The mixture was then cooled to 100° C. and poured into seven liters of water with stirring. Upon cooling, the product solidified into finely-granulated particles. This material was filtered and a very dark-colored wash water was separated by vacuum filtration. Washing was continued with several liters of water until the last portion of wash water was colorless. The solid, light amber in color, was spread on stainless steel trays and dried in a vacuum oven operated at 80° C. and then at 102° C.

EXAMPLE III

To a closed 12-liter reaction vessel 4764 grams of the alpha olefin mixture identified above and 993 grams of maleic anhydride were charged. The mixture was melted, flushed with nitrogen and heated at ambient pressure under nitrogen at 180° to 200° C. for 12 hours. Upon evacuation of the reaction mixture to 15 millimeters of mercury, a very small amount of anhydride was obtained. The mixture was cooled to 100° C. and poured into 20 liters of water. After cooling the product was separated by centrifuging and then repeatedly washed until the wash water was colorless and its pH was 7. The product, light amber in color, was dried in a vacuum oven at 80°–102° C. on stainless steel trays. The combined alkenyl succinic acid obtained from Examples II and III amounted to 7800 grams.

EXAMPLE IV

The combined product from Examples II and III were mixed and blended at 85° C. and the warm mixture was allowed to stand at 85° C. for 30 minutes. The molten blend was then decanted into trays, cooled and ground. Twenty-five grams of this material were azeotroped in 100 grams of xylene at a temperature of 135° C. and a pressure of 14.8 pounds per square inch gauge (1.04 kilograms per square centimeter), resulting in a loss of 1.2 grams of water. 23.5 grams of alkenyl succinic anhydride were obtained.

The fact that the dark-colored, impure alkenyl succinic product obtained above can be purified by merely treating the same with water is surprising. Since the alkenyl succinic product is waxy and obviously incompatible with water, it would not have been expected that efficient contact could be obtained between the two to effect the desired purification.

Obviously, many modifications and variations of the invention, as hereinabove set forth, can be made without departing from the spirit and scope thereof, and therefore only such limitations should be imposed as are indicated in the appended claims.

We claim:

1. A process for improving the color of the reaction product of an olefin with maleic anhydride which comprises reacting a straight or branched chain olefin having from 26 to 100 carbon atoms, said olefin having been obtained as a result of the polymerization of ethylene, with maleic anhydride in a temperature range of about 140° to about 250° C. for about three to about 60 hours to obtain an alkenyl succinic anhydride dark in color having the following structural formula:

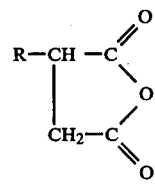

wherein R is an alkenyl group having from 26 to 100 carbon atoms, bringing the alkenyl succinic anhydride at a temperature of about 75° to about 150° C. into contact with water at a temperature of about 0° to about 80° C. wherein the amount of water used relative to said alkenyl succinic anhydride on a molar basis ranges from about 10:1 to about 1000:1, mechanically stirring the resulting mixture over a period of about one-half to about three hours while maintaining the temperature of the water within the range of about 10° to about 80° C., resulting in the solidification of the alkenyl succinic anhydride and the conversion thereof to the corresponding alkenyl succinic acid in particulate form, and then mechanically separating the water from the alkenyl succinic acid to obtain alkenyl succinic acid of improved color.

2. The process of claim 1 wherein said olefin has from 30 to 60 carbon atoms, the reaction temperature with maleic anhydride is in the range of about 180° to about 220° C. and the reaction time is about six to about 24 hours.

3. The process of claim 1 wherein the amount of water used relative to said alkenyl succinic anhydride on a molar basis ranges from about 50:1 to about 500:1.

4. The process of claim 1 wherein the temperature of said alkenyl succinic anhydride when the same is brought into contact with water is in the range of about 90° to about 120° C. and of the water about 5° to about 40° C., the stirring is carried out over a period of about one to about two hours and the temperature of the water is maintained in the range of about 20° to about 40° C.

5. The process of claim 1 wherein at the end of said treatment the alkenyl succinic acid is converted to the corresponding alkenyl succinic anhydride.

* * * * *